US00RE38103E

(19) United States

(12) Reissued Patent

Guay et al.

(10) Patent Number: US RE38,103 E

(45) Date of Reissued Patent: Apr. 29, 2003

(54) 5-METHANESULFONAMIDO-1-INDANONES AS AN INHIBITOR OF CYCLOOXYGENASE-2

(75) Inventors: Daniel Guay, Ile Perrot (CA); Chun-Sing Li, Dollard des Ormeaux (CA)

(73) Assignee: Merck Frosst Canada & Co., Rairkland (CA)

(21) Appl. No.: 09/827,508

(22) Filed: Apr. 6, 2001

Related U.S. Patent Documents

Reissue of:

(64) Patent No.: 5,604,260
Issued: Feb. 18, 1997
Appl. No.: 08/147,804
Filed: Nov. 4, 1993

U.S. Applications:

(63) Continuation-in-part of application No. 07/989,286, filed on Dec. 11, 1992, now abandoned, and application No. 08/033,397, filed on Mar. 19, 1993, now abandoned.

(51) Int. Cl.[7] ..... A61K 31/165; C07C 311/12

(52) U.S. Cl. ..... 514/605; 564/99; 514/601

(58) Field of Search ..... 514/605, 601; 564/99

(56) References Cited

U.S. PATENT DOCUMENTS

| | | | | | |
|---|---|---|---|---|---|
| 2,646,385 | A | * | 7/1953 | Lewenstein | 167/55 |
| 3,010,873 | A | * | 11/1961 | Cavallini et al. | 167/65 |
| 3,121,044 | A | * | 2/1964 | Buckwalter et al. | 167/82 |
| 3,128,226 | A | * | 4/1964 | Rubin et al. | 167/55 |
| 3,439,009 | A | * | 4/1969 | Emele | 424/253 |
| 3,840,597 | A | * | 10/1974 | Moore et al. | 260/556 |
| 4,244,960 | A | * | 1/1981 | Schroeder et al. | 424/263 |
| 4,375,479 | A | * | 3/1983 | Schroeder et al. | 424/321 |
| 4,820,827 | A | * | 4/1989 | Haber | 549/78 |
| 4,866,091 | A | * | 9/1989 | Matsuo et al. | 514/471 |
| 4,885,367 | A | * | 12/1989 | Yoshikawa et al. | 546/216 |
| 5,409,944 | A | * | 4/1995 | Black et al. | 514/359 |

FOREIGN PATENT DOCUMENTS

| | | | |
|---|---|---|---|
| JP | 130870/86 | * | 1/1986 |
| JP | 242997/90 | * | 4/1992 |

OTHER PUBLICATIONS

Boyce et al. Nueropharmacology. 1994. vol. 33, No. 12, pp. 1609–1611.*

Wisenberg–Bottcher et al. Agents and Actions. 1989. vol. 26, pp. 240–242.*

Lombardino et al. Arzneim.–Forsch. (Drug Res.) 1975. vol. 25, No. 10, pp. 1629–1635.*

Lombardino. Nonsteroidal Antiinflammatory Drugs. 1985. pp. 114–130.*

National Meeting of the American Chemical Society, Washington, D.C., USA, Aug. 21–25, 1994. Abstracts of Papers American Chemical Society. 208 (1–2), 1994 MEDI 272, ISSN: 0065–7727.*

National Meeting of the American Chemical Society, Washington, D.C., USA, Aug. 21–25, 1994. Abstracts of Papers American Chemical Society. 208 (1–2), 1994 MEDI 116, ISSN: 0065–7727.*

Chem Abstracts. 1983. vol. 100, No. 1, AB #6113u.*

D.P. Carr, et al., Agents and Actions, vol. 19, 5/6 (1986) pp. 374–375, "Comparison of the systemic inhibition of thromboxane synthesis, anti–inflammatory activity and gastro–intestinal toxicity . . .".*

Chem Abstracts. 1985. vol. 104, AB #107904r.*

Chem Abstracts. 1990. vol. 113, AB #224303r.*

Chem Abstracts. 1987. vol. 106, AB #60922u.*

Chem Abstracts. 1989. vol. 110, AB #128249v.*

Gans et al. Journal of Pharm. and Experim. Ther., 1990. vol. 254, No. 1, pp. 180–187.*

Hla et al. Proceedings of the National Academy of Sciences, USA. 1992. vol. 89, pp. 7384–7388.*

Rufer et al. European Journal of Med. Chem. Chim. Ther. 1982. vol. 17, pp. 173–180.*

* cited by examiner

*Primary Examiner*—Carla J. Myers

(74) *Attorney, Agent, or Firm*—Howrey Simon Arnold & White LLP

(57) ABSTRACT

The Compound of Formula I and pharmaceutically acceptable sales thereof in the treatment of cyclooxygenase-2 mediated diseases are disclosed.

I

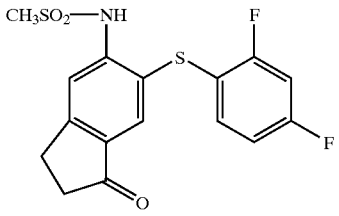

6 Claims, No Drawings

5-METHANESULFONAMIDO-1-INDANONES AS AN INHIBITOR OF CYCLOOXYGENASE-2

Matter enclosed in heavy brackets [ ] appears in the original patent but forms no part of this reissue specification; matter printed in italics indicates the additions made by reissue.

This is a continuation-in-part of U.S. Ser. No. 07/989,286 filed Dec. 11, 1992, now abandoned, and U.S. Ser. No. 08/033,397, filed Mar. 19, 1993, now abandoned.

BACKGROUND OF THE INVENTION

This invention relates to compounds and pharmaceutical compositions for the treatment of inflammation, particularly cyclooxygenase mediated diseases and methods of treating thereof.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for an inducible form of cyclooxygenase (cyclooxygenase-2) has been cloned, sequenced and characterized from chicken, mu-rine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties of a conventional non-steroidal antiinflammatory drug (NSAID), and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and a lessened ability to induce asthma attacks in aspirin-sensitive asthmatic subjects.

SUMMARY OF THE INVENTION

The invention encompasses compounds of Formula I useful in the treatment of inflammation such as cyclooxygenase mediated diseases, particularly cyclooxygenase-2 mediated diseases.

I

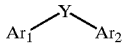

The invention also encompasses methods of treating inflammation including cyclooxygenase mediated diseases, particularly cyclooxygenase-2 mediated diseases comprising: administration to a patient in need of such treatment of a non-toxic therapeutically effective amount of a compound of Formula I.

I

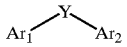

The invention also encompasses certain pharmaceutical compositions for treatment of inflammation including cyclooxygenase mediated diseases, particularly cyclooxygenase-2 mediated diseases comprising compounds of Formula I and a pharmaceutically acceptable carrier.

The invention also encompasses the compound 12

12

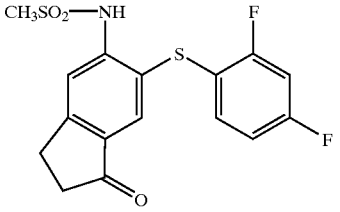

and pharmaceutically acceptable salts thereof which are useful in the treatment of inflammation such as cyclooxygenase mediated diseases, in particular cyclooxygenase-2 mediated diseases.

The invention also encompasses anti-inflammatory pharmaceutical compositions such as those useful for inhibiting a cyclooxygenase and for treating cyclooxygenase mediated diseases as disclosed herein comprising a pharmaceutically acceptable carrier and a non-toxic therapeutically effective amount of the compound of Formula I as described herein.

The pharmaceutical compositions of the present invention comprise a compound of Formulas I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including s inorganic bases and organic bases. Salts derived from inorganic bases include aluminum, ammonium, calcium, copper, ferric, ferrous, lithium, magnesium, manganic salts, manganous, potassium sodium, zinc and the like. Particularly preferred are the ammonium, calcium, magnesium, potassium, and sodium salts. Salts derived from o pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline,-N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylgncamine, morpholine, piperazine, piperdine, polyamine resins, procaine, purines, theobromine, triethylamine, trimethylamine, tripropylamine, tromethamine, and the like.

The invention also encompasses methods of inhibiting cyclooxygenase and treating cyclooxygenase mediated diseases comprising: administration to a patient in need of such treatment of a non-toxic therapeutically effective amount of compound of Formula I as disclosed herein.

It will be understood that in the discussion of methods of treatment which follows, references to the compound of Formula I are meant to also include the pharmaceutically acceptable salts.

DETAILED DESCRIPTION OF THE INVENTION

The invention encompasses compounds of Formula I useful in the treatment of inflammation such as cyclooxygenase mediated diseases, particularly cyclooxygenase-2 mediated diseases

I

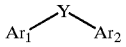

wherein Y is O, S, S(O), $S(O)_2$, —$CH_2$—, —NH—, CO or

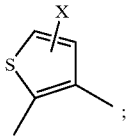

X is H, halo, including Cl and Br, or $C_{1-6}$alkyl; and $Ar_1$ and $Ar_2$ are as defined below in the following five embodiments.

In one embodiment the invention encompasses compounds of Formula I wherein Y is

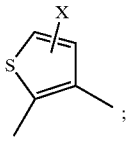

$Ar_1$ is

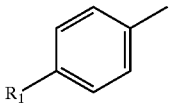

$Ar_2$ is

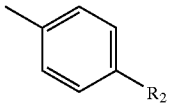

wherein $R_1$ and $R_2$ are each independently selected from the group consisting of (a) $NHS(O)_2C_{1-6}$alkyl, (b) halo, including Fluoro, (c) $C_{1-6}$alkyl, (d) $S(O)_2C_{1-6}$alkyl, (e) $OC_{1-6}$alkyl, and (f) hydrogen, with the proviso that $R_1$ and $R_2$ are not simultaneously the same.

In a second embodiment, the invention encompasses compounds of Formula I wherein wherein Y is O, S, S(O), $S(O)_2$, —$CH_2$—, —NH— or CO, preferably S or O; $Ar_1$ is

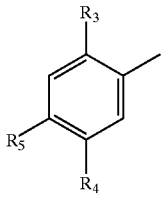

$Ar_2$ is a group selected from the group consisting of:

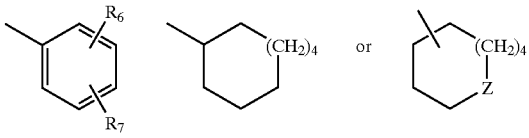

wherein $R_3$ is $NHS(O)_2C_{1-6}$alkyl, $NHS(O)_2CF_3$, or $N(CH_3CO)S(O)_2CH_3$;

$R_4$ is selected from the group consisting of (a) acyl such as CO—$C_{1-3}$alkyl, (b) cyano, (c) carboxy;

(d) carboxy $C_{1-6}$alkyl ester, (e) carboxamide, (f) $C_{1-6}$alkyl sulfinyl, (g) $C_{1-6}$alkyl sulfonyl, and (h) nitro;

$R_5$ is H, $C_{1-3}$alkyl, or $R_4$ and $R_5$ are joined together to form a saturated monocyclic ring of five (5) carbons, wherein one of the carbons is substituted with an oxo or oximino group, or one of the carbons may be replaced by $S(O)_2$;

$R_6$ and $R_7$ are each independently selected from the group consisting of hydrogen, $C_{1-3}$alkyl or halo, including fluoro;

n is 0, 1, or 2; and

Z is O or S.

In a third embodiment the invention encompasses compounds of formula I wherein

Y is O;

$Ar_1$ is

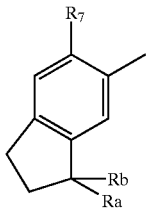

$R_7$ is a group such as (a) $NHS(O)_2C_{1-6}$alkyl, (b) $N(CH_3CO)S(O)_2CH_3$, or (c) $NHS(O)_2CF_3$; and Ra and Rb are jointly oxo or oximino;

$Ar_2$ is

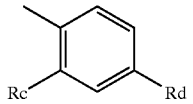

wherein Rc and Rd are each independently selected from hydrogen or halo, such as fluoro, Cl, Br, or Iodo.

With regard to the third embodiment $Ar_2$ may alteratively be tri substituted with substituents independently selected from:

(a) hydrogen, (b) F, Cl, Br, or I, (c) methyl or ethyl, (d) $—CF_3$, (e) vinyl or —C≡CH, (f) $—OCH_3$ or $—OCF_3$, (g) $SCH_3$ or $SCF_3$, (h) CN, or (i) $N_3$, the substitutents residing at position 1, 3 and 5 of the phenyl.

Thus one alternative to this third embodiment is the compounds of Formula I

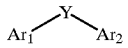

wherein $Ar_1$ is

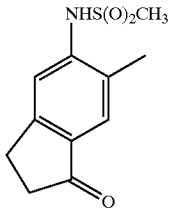

Y is O or S; and $Ar_2$ is

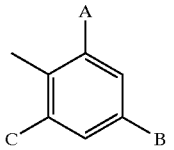

wherein A, B and C are each independently selected from (a) hydrogen, (b) F, CI, Br, or I, (c) methyl or ethyl, (d) $—CF_3$, (e) vinyl or —C≡CH, (f) $—OCH_3$ or $—OCF_3$, (g) $SCH_3$ or $SCF_3$, (h) CN, or (i) $N_3$.

In a fourth embodiment the invention encompasses compounds of Formula I wherein

Y is O or S;

$Ar_1$ is

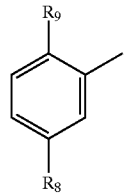

wherein $R_9$ is a group such as $R_xS(O)2NR$, wherein $R_x$ is $C_{1-3}$alkyl or $CF_3$, and R is hydrogen or a pharmaceutically acceptable cation;

$R_8$ is nitro or acyl, such as CO—$C_{1-3}$alkyl;

$Ar_2$ is

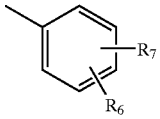

$R_6$ and $R_7$ are each independently selected from the group consisting of hydrogen, $C_{1-3}$alkyl or halo, including fluoro;

In a fifth embodiment the invention encompasses compounds of Formula I wherein $Ar_1$ is

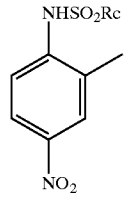

Re is $C_{1-3}$alkyl or trifluoromethyl;

Y is O, S, S(O), or $S(O)_2$; and $Ar_2$ is

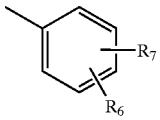

wherein $R_6$ and $R_7$ are each independently selected from the group consisting of hydrogen, Cl-3alkyl or halo, including fluoro; or $Ar_2$ is

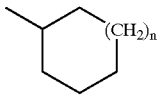

wherein n is 0, 1, or 2.

Exemplifying this aspect of the invention are the following compounds:

A

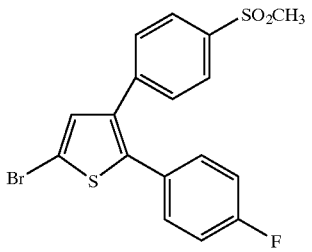

B

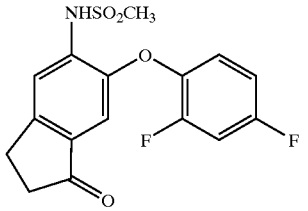

C

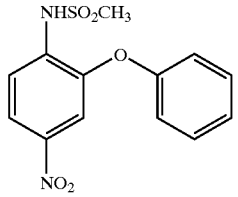

D

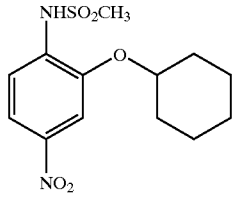

as well as compound compound 12 mentioned above

12

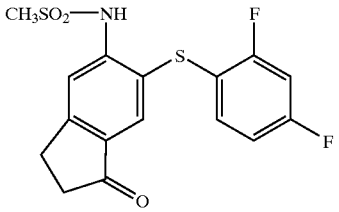

and pharmaceutically acceptable salts thereof.

A is appreciated by thoses of skill in the art, compounds A to D are known by the names Dup 697 (compound A), Flosulide (compound B), Nimesulide (compound C), and NS 398 (compound D).

Illustrative of the pharmaceutically acceptable salts is the formula

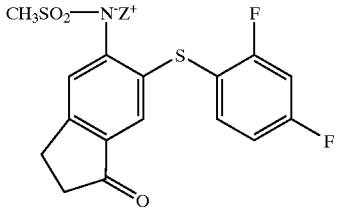

wherein $Z^+$ is a pharmaceutically acceptable counterion. As is well appreciated by those of skill in the an, the pharmaceutically acceptable counterions include, aluminum, calcium, lithium, magnesium, potassium, sodium, barium, zinc, ammonium, or an amino acid such as glycine, alinine, valine, leucine, isoleucine, serine, threonine, aspartic acid, asparagine, glutamic acid, lysine, hydroxylsine, histidine, arginine, phenylalanine, tyrosine, tryptophan, thyroxine, cystine, x s cysteine, methionine, proline, hydroxyproline, ornithine, b-alanine, a-amino butyric acid, sarcosine, betaine, homoserine, and citrulline, or mono, di, or tri$C_{1-6}$alkylamino.

The invention also encompasses anti-inflammatory pharmaceutical compositions such as for inhibiting cyclooxygenase and for treating cyclooxygenase mediated diseases as disclosed herein comprising a pharmaceutically acceptable carrier and a non-toxic therapeutically effective amount of compound of Formula I as described above.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of compound of Formula I as described above.

The invention also encompasses a method of inflammation such as inhibiting cyclooxygenase (e.g. cyclooxygenase-2) and treating cyclooxygenase (e.g. cycloxygenase-2) mediated diseases as disclosed herein comprising: administration to a patient in need of such treatment of a non-toxic therapeutically effective amount of compound of Formula I as described above.

Within this embodiment the invention encompasses a method of selectively inhibiting cyclooxygenase-2 and selectively treating cyclooxygenase-2 mediated diseases as disclosed herein comprising: administration to a patient in need of such treatment of a non-toxic therapeutically effective amount of compound of Formula I as disclosed herein. For purpose of this specification a compound that is selective for the inhibition of cyclooxygenase-2 or for treatment of cyclooxygenase-2 mediated diseases is a compound that demonstrates an in vitro or in vivo $IC_{50}$ ratio for COX-1 to COX-2 of approximately 1000 or greater.

As disclosed elsewhere in this specification in further detail, these diseases include pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries.

The compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursiris, bums, injuries, following surgical and dental procedures. In addition, such a compound may inhibit cellular neoplastic transformations and metastic tumor growth and hence can be used in the treatment of cancer. The compounds of Formula I will also inhibit prostanoid-induced smooth muscle contraction by preventing the synthesis of contractile prostanoids and hence may be of use in the treatment of dysmenorrhea, premature labor and asthma. Compounds of formula 1 may also be useful in the treatment of Alzheimers disease and menentia.

By virtue of their high cyclooxygenase-2 (COX-2) activity and/or their specificity for cyclooxygenase-2 over cyclooxygenase-1 (COX-1), the compound of Formula I will prove useful as alternatives to conventional non-steroidal anti-inflammatory drugs (NSAID'S) particularly where such non-steroidal anti-inflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, the compound of Formula I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetaminophen or phenacetin; a potentiator including caffeine; an H2-antagonist, aluminum or magnesium hydroxide, simethicone, a decongestant including phenylephrine, phenylpropanolamine, s pseudophedrine, oxymetazoline, ephinephrine, naphazoline, xylometazoline, propylhexedrine, or levo-desoxyephedrine; an antitussive including codeine, hydrocodone, caramiphen, carbetapentane, or dextramethorphan; a diuretic; a sedating or nonsedating antihistamine. In addition the invention encompasses a method of treating cyclooxygenase mediated diseases comprising: administration to a patient in need of such treatment a non-toxic therapeutically effective amount of compound of Formula I, optionally co-administered with one or more of such ingredients as listed immediately above.

The compounds of the present invention is an inhibitor of cyclooxygenase-2 and is thereby useful in the treatment of cyclooxygenase-2 mediated diseases as enumerated above. This activity is illustrated by it's ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I. The IC50 values represent the concentration of inhibitor required to return $PGE_2$ synthesis to 50% of that obtained as compared to the uninhibited control. Illustrating this aspect, is the a comparison is provided hereinunder of the compound 12 with Flosulide:

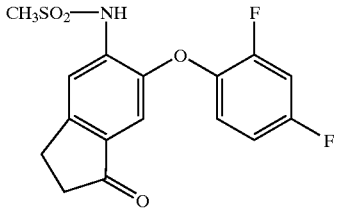

Flosulide

This compound and it's method of preparation is disclosed in U.S. Pat. No. 4,375,479, issued to Schroeder, et al., Mar. 1, 1983.

By way of comparison, Ibuprofen has an IC50 for COX-2 of 1 mM, and Indomethacin has an $IC_{50}$ for COX-2 of approximately 100 nM.

For the treatment of any of these cyclooxygenase mediated diseases the compound of Formula I and pharmaceutically accetable salts thereof may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques. In addition to the treatment of warm-blooded animals such as mice, rats, horses, cattle, sheep, dogs, cats, etc., the compounds of the invention are effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the an for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycertanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable Oil, for example arachis oil, olive oil, sesame oil or coconut oil, or in a mineral oil such as liquid paraffin. s The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known an using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fattyacids such as oleic acid find use in the preparation of injectables.

The compound of Formula (I) and pharmaceutically acceptable salts thereof may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula (I) are employed. (For purposes of this application, topical application shall include mouth washes and gargles.)

Dosage levels of the order of from about 0.01 mg to about 140 mg per kilogram of body weight per day are useful in the treatment of the above-indicated conditions, or alternatively about 0.5 mg to about 7 g. per patient per day. For example, inflammation may be effectively treated by the administration of from about 0.01 to 50 mg of the compound per kilogram of body weight per day, or alternatively about 0.5 mg to about 1.0 g per patient per day. A typical dosage range is 100 or 200 mg to about 1000 mg. An upper ranges of 500 or 2000 mg is also be regarded as typical.

The amount of active ingredient that may be combined with the carder materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 1000 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Compounds of the instant invention are conveniently prepared using the procedures described in the methods below. Additional relevant chemistry is described in U.S. Pat. No. 4,375,479, issued to Schroeder, et al., Mar. 1, 1983 which is hereby incorporated by reference.

METHOD A

5-Aminoindane II is acetylated, followed by bromination to give the 5-acetylamino-6-bromoindane III. Oxidation with chromium trioxide in aqueous acetic acid, followed by acidic hydrolysis gives the 5-amino-6-bromo-1-indanone IV. The amino group is converted to the nitro group by diazotization followed by treatment of the corresponding diazonium salt with sodium nitrite in the presence of copper powder. Subsequent protection of the carbonyl as a dioxolane provides 5-nitro-6-bromo-1-indanone ethylene ketal V. Coupling with an appropriate s nucleophile proceeds under basic conditions with or without the presence of a copper salt. Reduction of the nitro group with iron powder or tin(II) chloride in aqueous ethanol with concomitant hydrolysis of the ketal group leads to amino indanone VI.

Sulfonylation with excess methanesulfonyl chloride in the presence of trimetylamine yields the corresponding bissulfonamide, which upon subsequent hydrolysis with sodium hydroxide yields the title compound I'.

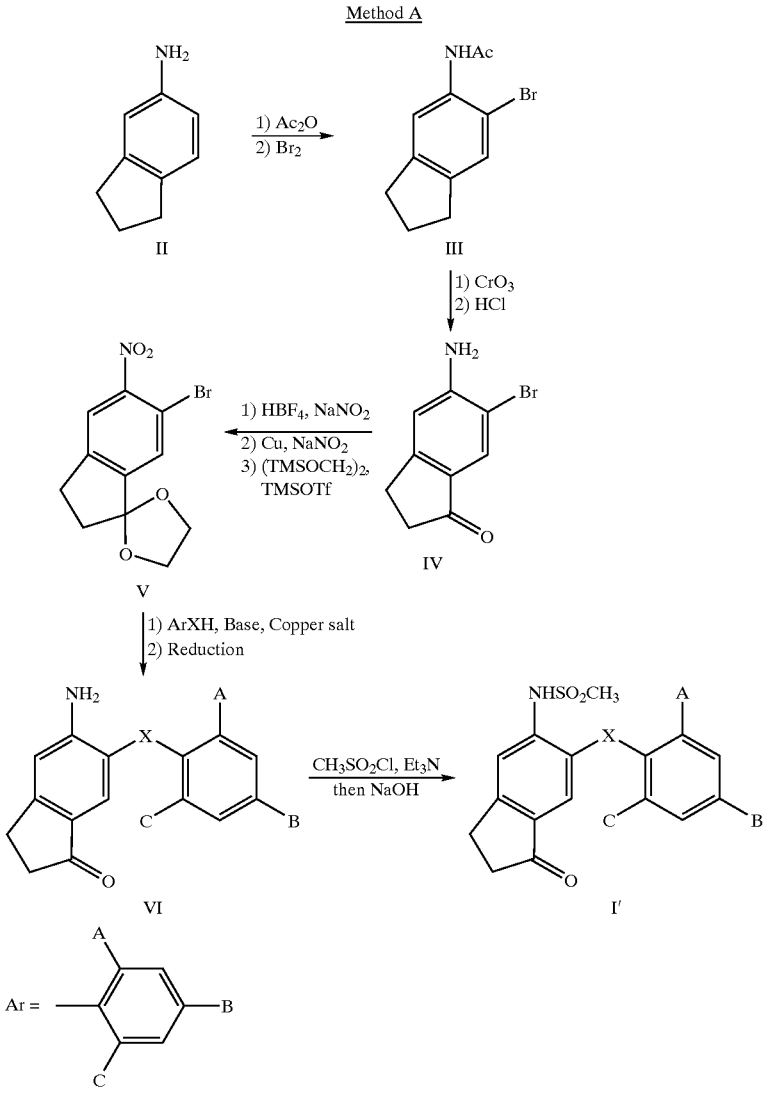

METHOD B

4-Chloro-3-nitrobenzaldehyde is coupled with an appropriate nucleophile under basic conditions to give VII. Reduction of the nitro groups with iron powder of tin/II chloride in aqueous ethanol gives the corresponding aniline, which is converted to the bissulfonamide with excess methanesulfonyl chloride in the presence of triethylamine. Basic hydrolysis of the bissulfonamide then yields IX. A two carbon elongation step with triethyl phosphonoacetate anion (prepared from treatment with sodium hydride) or (carbethoxymetylene)triphenylphosphorane provides an α, β-unsaturated ester. Reduction of the double bond with 10% palladium on charocoal under hydrogen atmosphere followed by ester hydrolysis affords acid X. The acid X is converted to the acid chloride and then treated with aluminum chloride or other standard Friedel-Crafts Lewis acid catalysts to give the title compound I'.

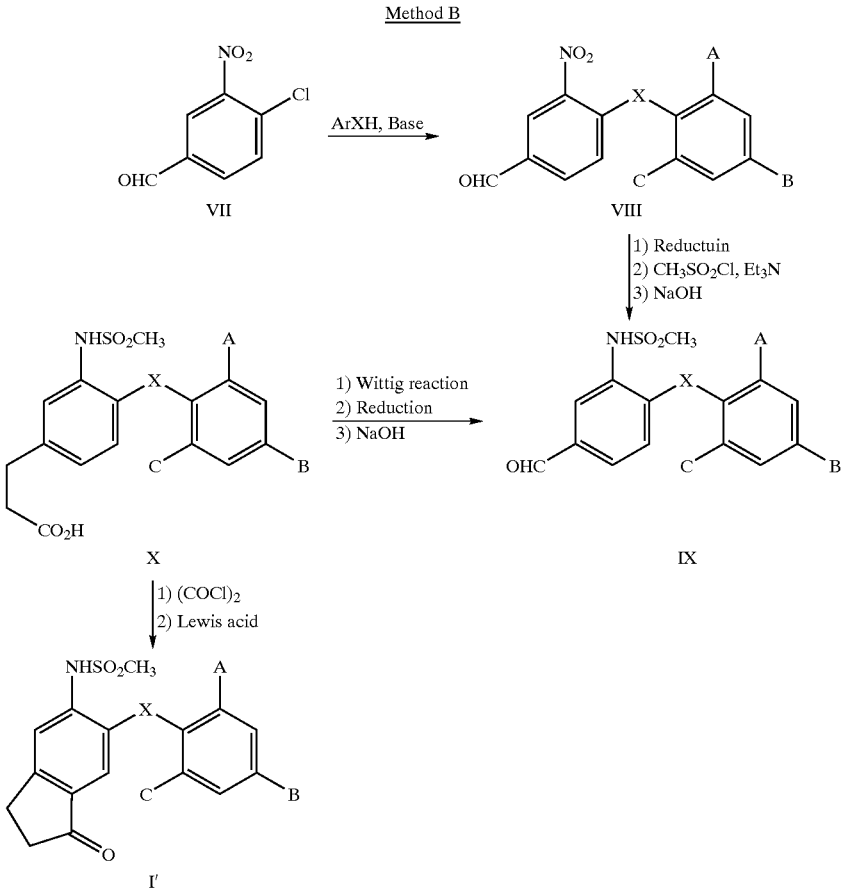

ASSAYS FOR DETERMINING BIOLOGICAL ACTIVITY

The compound of Formula I were tested using the following assays to determine their cyclooxygenase-2 inhibiting activity.

INHIBITION OF CYCLOOXYGENASE ACTIVITY

Compounds were tested as inhibitors of cyclooxygenase activity in whole cell and microsomal cyclooxygenase assays. Both of these assays measured prostaglandin $E_2$ synthesis in response to arachidonic acid, using a radioimmunoassay. Cells used for whole cell assays, and from which microsomes were prepared for microsomal assays, were human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition.

RAT PAW EDEMA ASSAY—PROTOCOL

Male Sprague-Dawley rats (150–200 g) were fasted overnight and were given po either vehicle (1% methocel) or a test compound. One hr later, a line was drawn using a permanent marker at the level above the ankle in one hind paw to define the area of the paw to be monitored. The paw volume ($V_O$) was measured using a plethysmometer (Ugo-Basile, Italy) based on the principle of water displacement. The animals were then injected subplantarly with 50 $\mu$l of 1% carrageenan solution in saline (FMC Corp, Maine) into the paw using an insulin syringe with a 25 -gauge needle (i.e. 500 $\mu$g carrageenan per paw). Three hr later, the paw volume ($V_3$) was measured and the increases in paw volume ($V_3$–$V_0$) were calculated. The animals were sacrificed by $CO_2$ aphyxiation and the absence or presence of stomach lesions scored. Data were compared with the vehicle-control values and percent inhibition calculated. Since a maximum of 60–70% inhibition (paw edema) was obtained with standard NSAIDs, $ED_{30}$ values were used for comparison and at at least 3 different concentrations. At least 6 animals were used at each concentration All treatment groups were coded to eliminate observer bias.

REPRESENTATIVE BIOLOGICAL DATA

The compounds of the present invention are inhibitors of cyclooxygenase-2 and are thereby useful in the treatment of inflammation such cyclooxygenase-2 mediated diseases as enumerated above. The activities of the compound against cyclooxygenase may be seen in the representative results shown below. In the assay, inhibition is determined by measuring the amount of prostaglandin $E_2$ ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control.

The results for inhibition of $PGE_2$ production may be seen in the following Table.

COMPARISON OF SELECTED COMPOUNDS WITH FLOSULIDE

| | CONC (nM) | COX-2 % INHB | COX-1 % INHB | Rat Paw EDEMA $ED_{30}$ (mpk) | Rat Plasma Levels @ 1 hr (μg/ml) | Monkey $C_{max}$ (μg/ml) | t½ Monkey (n = 2) (Estimated) |
|---|---|---|---|---|---|---|---|
| INDOMETHACIN | $IC_{50}$ | 50 nM | 10 nM | 1.1 ± .3 | | | |
| 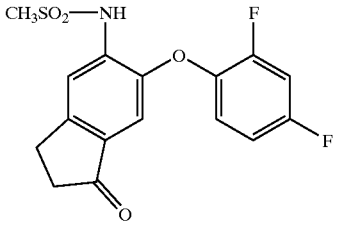 Flosulide | $IC_{50}$ | 50 nM | Inactive at 50 μM | 1.1 ± .4 | 48 @ 20 mpk | 17 @ 10 mpk | <4 hr |
| 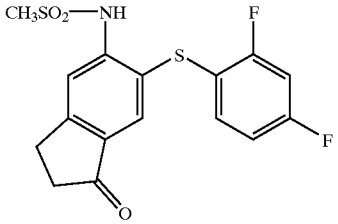 12 | 10<br>100<br>1000 | 43<br>87<br>91 | Inactive at 10 μM | 0.3 ± .1 | 70 @ 10 mpk | 35 @ 5 mpk | >9 hr |
| 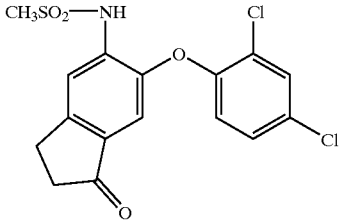 4 | $IC_{50}$ | 8 nM | Inactive at 100 μM | 0.22 | | | |
| 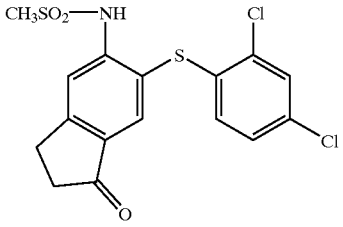 17 | $IC_{50}$ | 7 nM | | 0.1 | | | |

BIOLOGICAL ACTIVITIES OF PREPARED EXAMPLES

| Compound # | COX-2 $IC_{50}$ (nM) | COX-1 $IC_{50}$ (nM) | Rat Paw Edema $ED_{50}$ (mpk) |
|---|---|---|---|
| 1 | 30 | | Schering U.S. Pat. No. 4,244,960 |
| 2 | 9 | | |
| 3 (Flosulide) | 50 | >50,000 | 0.62 Schering U.S. Pat. No. 4,375,479 |
| 4 | 8 | >100,000 | 0.22 |
| 5 | 100 | | |

-continued

BIOLOGICAL ACTIVITIES OF PREPARED EXAMPLES

| Compound # | COX-2 $IC_{50}$ (nM) | COX-1 $IC_{50}$ (nM) | Rat Paw Edema $ED_{50}$ (mpk) |
|---|---|---|---|
| 6 | 50 | >100,000 | 0.16 |
| 7 | 100 | | |
| 8 | 100 | | |
| 9 | 100 | | |
| 10 | 8 | >10,000 | 3.0 |
| 11 | 10 | | |
| 12 | 50 | >10,000 | 0.3 |

-continued

BIOLOGICAL ACTIVITIES OF PREPARED EXAMPLES

| Compound # | COX-2 $IC_{50}$ (nM) | COX-1 $IC_{50}$ (nM) | Rat Paw Edema $ED_{50}$ (mpk) |
|---|---|---|---|
| 13 | 100 | | |
| 14 | 13 | | |
| 15 | 10 | | |
| 16 | 11 | | |
| 17 | 7 | | |
| 18 | 60 | >100,000 | |
| 19 | 100 | | |
| 20 | 50 | | |
| 21 | 100 | | |
| 22 | 50 | | |
| 23 | 300 | | |
| 24 | 100 | | |
| 25 | 1,000 | | |

NMR DATA FOR EXAMPLES

| Compound # | X | A | B | C | NMR δ (ppm) |
|---|---|---|---|---|---|
| 1 | O | H | H | H | See U.S. Pat. No. 4,244,960 |
| 2 | O | H | Br | H | ($CDCl_3$) 7.73(s, 1H), 7.53(d, 2H), 7.29(m, 1H), 7.14(s, 1H), 6.94(d, 2H), 3.16(s, 3H), 3.13(t, 2H), 2.70(t, 2H). |
| 3 | O | F | F | H | See U.S. Pat. No. 4,375,479 |
| 4 | O | Cl | Cl | H | ($CDCl_3$) 7.73(s, 1H), 7.50(s, 1H), 7.32(m, 2H), 7.08(d, 1H), 6.90(s, 1H), 3.14(s, 3H), 3.10(t, 2H), 2.68(t, 2H). |
| 5 | O | H | SMe | H | (Acetone-$d_6$) 8.65(brs, 1H), 7.79(s, 1H), 7.38(d, 2H), 7.08(d, 2H), 7.01(s, 1H), 3.20(s, 3H), 3.14(t, 2H), 2.62(t, 2H), 2.50(s, 3H). |
| 6 | S | H | H | H | ($CDCl_3$) 8.08(s, 1H), 7.85(s, 1H), 7.80(s, 1H), 7.32–7.10(m, 5H), 3.20(t, 2H), 2.78(s, 3H), 2.74(t, 2H). |
| 7 | S | F | H | H | ($CDCl_3$) 8.02(s, 1H), 7.97(brs, 1H), 7.28(m, 1H) 7.15(t, 1H), 7.08(m, 2H), 3.13(t, 2H), 2.97(s, 3H), 2.70(t, 2H). |
| 8 | S | H | F | H | ($CDCl_3$) 8.00(s, 1H), 7.80(s, 1H), 7.76(s, 1H) 7.16(t, 2H), 6.98(t, 2H), 3.16(t, 2H), 2.88(s, 3H), 2.72(t, 2H). |
| 9 | S | H | Cl | H | ($CDCl_3$) 8.04(s, 1H), 7.82(brs, 2H), 7.25(d, 2H), 7.08(d, 2H), 3.20(t, 2H), 2.92(s, 3H), 2.75(t, 2H). |
| 10 | S | H | Br | H | (Acetone-$d_6$) 9.15(brs, 1H), 7.75(s, 1H), 7.65(s, 1H), 7.54(d, 2H), 7.22(d, 2H), 3.18(t, 2H), 3.10(s, 3H), 2.65(t, 2H). |
| 11 | S | H | I | H | ($CDCl_3$) 8.03(s, 1H), 7.78(brs, 2H), 7.56(d, 2H), 6.82(d, 2H), 3.18(t, 2H), 2.88(s, 3H), 2.71(t, 2H). |
| 12 | S | F | F | H | ($CDCl_3$) 8.05(s, 1H), 7.98(s, 1H), 7.78(s, 1H), 7.30(m, 1H), 6.88(m, 2H), 3.16(t, 2H), 3.06(s, 3H), 2.70(t, 2H). |
| 13 | S | F | H | F | ($CDCl_3$) 8.22(brs, 1H), 8.03(s, 1H), 7.72(s, 1H), 7.32(m, 1H), 6.96(m, 2H), 3.11(t, 2H), 3.05(s, 3H), 2.65(t, 2H). |
| 14 | S | F | Cl | H | ($CDCl_3$) 7.97(s, 1H), 7.92(bs, 1H), 7.75(s, 1H) 7.08(m, 3H), 3.14(t, 2H), 3.30(s, 3H), 2.70(t, 2H). |
| 15 | S | F | Br | H | ($CDCl_3$) 7.97(s, 1H), 7.91(brs, 1H), 7.77(s, 1H) 7.23(m, 2H), 7.00(t, 1H), 3.13(t, 2H), 3.03(s, 3H) 2.70(t, 2H). |
| 16 | S | Cl | F | H | ($CDCl_3$) 7.97(s, 1H), 7.82(brs, 1H), 7.78(s, 1H), 7.19(m, 1H), 6.88(d, 2H), 3.18(t, 2H), 3.00(s, 3H), 2.71(t, 2H). |
| 17 | S | Cl | Cl | H | ($CDCl_3$) 8.00(s, 1H), 7.82(s, 1H), 7.78(s, 1H), 7.46(d, 1H), 7.10(dd, 1H), 6.68(d, 1H), 3.20(t, 2H), 3.02(s, 3H), 2.78(t, 3H). |
| 18 | S | F | Br | F | ($CDCl_3$) 8.18(brs, 1H), 8.03(s, 1H), 7.74(s, 1H), 7.16(d, 2H), 3.14(t, 2H), 3.11(s, 3H), 2.69(t, 2H). |
| 19 | S | $CH_3$ | H | H | ($CDCl_3$) 7.97(s, 1H), 7.82(s, 1H), 7.68(brs, 1H), 7.23(d, 1H), 7.15(t, 1H), 7.05(t, 1H), 6.76(d, 1H), 3.18(t, 2H), 2.82(s, 3H), 2.75(t, 2H). |
| 20 | S | H | $CH_3$ | H | ($CDCl_3$) 8.04(s, 1H), 7.82(s, 1H), 7.78(s, 1H), 7.10(s, 4H), 3.16(t, 2H), 2.78(s, 3H), 2.72(t, H), 2.30(s, 3H). |
| 21 | S | $CF_3$ | H | H | ($CDCl_3$) 8.05(s, 1H), 7.81(s, 1H), 7.74(s, 1H), 7.70(d, 1H), 7.30(m, 2H), 6.92(d, 1H), 3.18(t, 2H), 2.86(s, 3H), 2.73(t, 2H). |
| 22 | S | H | $CF_3$ | H | ($CDCl_3$) 8.06(s, 1H), 7.85(s, 1H), 7.80(brs, 1H), 7.52(d, 2H), 7.16(d, 2H), 3.23(t, 2H), 2.97(s, 3H), 2.78(t, 2H). |
| 23 | S | H | $OCH_3$ | H | ($CDCl_3$) 7.98(s, 1H), 7.80(brs, 1H), 7.72(s, 1H), 7.20(d, 2H), 6.72(d, 2H), 3.76(s, 3H), 3.13(t, 2H), 2.79(s, 3H), 2.69(t, 2H). |

-continued

NMR DATA FOR EXAMPLES

| Compound # | X | A | B | C | NMR δ (ppm) |
|---|---|---|---|---|---|
| 24 | S | H | CH=CH$_2$ | H | (CDCl$_3$) 8.06(s, 1H), 7.84(s, 1H), 7.82(s, 1H), 7.31(m, 2H), 7.12(m, 2H), 6.65(q, 1H), 5.72(d, 1H), 5.28(d, 1H), 3.18(t, 2H), 2.80(s, 3H), 2.75(t, 2H). |
| 25 | S | H | Et | H | (CDCl$_3$) 8.04(s, 1H), 7.80(brs, 1H), 7.77(s, 1H), 7.12(s, 4H), 3.18(t, 2H), 2.77(s, 3H), 2.73(t, 2H), 2.61(q, 2H), 1.19(t, 3H). |

EXAMPLES

The invention is illustrated by the following non-limiting examples. Unless stated otherwide it is to be understood that (i) all operations were carried out at room or ambient temperature, that is, at a temperature in the range 18°–25° C.; (ii) evaporation of solvent was carded out using a rotary evaporator under reduced pressure (600–4000 pascals: 4.5–30 mm. Hg) with a bath temperature of up to 60° C.; (iii) the course of reactions was followed by thin layer chromatography (TLC) and reaction times are given for illustration only; (iv) melting points are uncorrected and 'd' indicates decomposition; the melting points given are those obtained for the materials prepared as described; polymorphism may result in isolation of materials with different melting points in some preparations; (v) the structure and purity of all final products were assured by at least one of the following techniques: TLC, mass spectrometry, nuclear magnetic resonance (NMR) spectrometry or microanalytical data; (vi) yields are given for illustration only; (vii) when given, NMR data is in the form of delta (d) values for major diagnostic protons, given in pans per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; and (viii) chemical symbols have their usual meanings; the following abbreviations have also been used v (volume), w (weight), b.p. (boiling point), m.p. (melting point), L (liter(s)), mL (milliliters), g (gram (s)), mg (milligram(s)), mol (moles), mmol (millimoles), eq (equivalent(s)).

PREPARATION EXAMPLE FOR METHOD A (COMPOUND 12)

5-Methanesulfonamido-6-(2,4-difluorophenylthio)-1-indanone

Step 1: 5-Acethylamninoindane

To a solution of 5 -aminoindane (10.0 g, 7.5 mmol) in $CH_2Cl_2$ (100 mL) was added dropwise acetic anhydride (9.2 g, 9.0 mmol) over a period of 15 min. After further stirring for 30 min, the mixture was quenched with 1M aqueous NaOH (100 mL). The $CH_2Cl_2$ layer was separated, washed successively with 1M aqueous HCl, brine, and was then dried over anhydrous $MgSO_4$ and concentrated in vacuo. Chromatography over silica gel, eluting with ethyl acetate-:hexanes (1:1) afforded 12.2 g (85%) of the title compound as a light brown powder. $^1$H NMR (CDCl$_3$): δ7.44 (1H, s), 7.12 (3H, three overlapping s), 2.88 (4H, m), 2.15 (3H, s), 2.06 (2H, m).

Step 2: 5-Acetylamino-6-bromoindane

To a solution of 5-acetylaminoindane (53.0 g, 0.30 mol) in glacial acetic acid (1 L) at 10° C. was added dropwise over a period of 1 h a solution of bromine (19.0 mL, 0.37 mol). The mixture was further stirred at 10° C. for 15 min, and was then diluted with water until no more precipitate formed. The precipitate was collected, washed with water and dried under vacuum to give 61 g (80%) of the title compound.

$^1$H NMR (CDCl$_3$): δ5 8.14 (1H, s), 7.50 (1H, s), 7.38 (1H, s), 7.38 (4H, m), 2.20 (3H, s), 2.08 (2H, m).

Step 3: 5-Acetylamino-6-bromo-1-indanone

To a solution of 5-acetylamino-6-bromoindane (43.0 g, 0.17 mol) in glacial acetic acid (400 mL) at 50°–55° C. was added dropwise a solution of chromium trioxide (70.0 g, 0,7 mol) in 50% aqueous acetic acid (400 mL) over a period of 30 min. After further stirring for 15 min, the mixture was cooled to 0° C. and quenched with 2-propanol (100 mL). Solvent was removed in vacuo. The residue was diluted with water (1 L) and extracted with ethyl acetate (2×500 mL). The combined ethyl acetate layer was washed with 0.5M aqueous NaOH (1 L), brine, dried over anhydrous $MgSO_4$ and concentrated to give 36 g (80%) of the title compound as a light brown solid which was contaminated with about 10% of 5-bromo-6-acetylamino- 1-indanone. $^1$H NMR (CDCl$_3$); δ8.60 (1H, s), 7.90 (1H, s), 7.90 (1H, s), 3.10 (2H, t), 2.70 (2H, t), 2.30 (3H, s).

Step 4: 5-Amino-6-bromo-1-indanone

A mixture of 5-acetylamino-6-bromo-1-indanone (36.0 g, 0.13 mol) and 6M aqueous hydrochloric acid (800 mL) was refluxed for 1 h. The homogenous solution was then cooled to 0° C. and adjusted to pH 8 with 10M aqueous NaOH (–480 mL). The precipitate formed was collected, washed with water and dried under vacuum to afford 30.0 g (quantitative) of the title compound as a light brown powder. $^1$H NMR (acetone-d$_6$): δ7.65 (1H, s), 6.90 (1H, s), 5.80 (2H, br s), 2.95 (2H, t), 2.50 (2H, t).

Step 5: 5-Nitro-6-bromo-1-indanone

To a suspension of 5-amino-6-bromo-1-indanone (30.0 g, 0.13 mol) in 20% aqueous fluoroboric acid (120 mL) at 0° C. was added dropwise 4M aqueous $NaNO_2$ (50 mL, 0.20 mol) over a period of 30 min. The mixture was stirred for 30 min after completion of addition. The resulting foamy suspension was added portionwise to a vigorously stirred mixture of copper powder (40 g, 0.62 mol) and sodium nitrite (120 g, 1.74 mol) in water (240 mL) at room temperature over a period of 15 min. During the addition, excessive foaming was broken up by the addition of small amounts of diethyl ether. After further stirring for 30 min, the mixture was filtered through celite, washed with ethyl acetate (5'300 mL). The ethyl acetate layer was separated, washed with brine, dried over anhydrous $MgSO_4$ and concentrated in vacuo. Chromatography over silica gel, eluting with $CH_2Cl_2$, yielded 17.5 g (51%) of the title compound as a pale yellow solid.

$^1$H NMR (CDCl$_3$); δ8.10 (1H, s), 7.85 (1H, s), 3.20 (2H, t), 2.85 (2H, t); mass spectrum (DCI, $CH_4$) m/e 256 ($M^+$+H).

Step 6: 5-Nitro-6-bromo-1-indanone ethylene ketal.

To a suspension of 5-nitro-6-bromo-1-indanone (11.0 g, 43 mmol) and bis(trhnethylsilyloxy)ethane (22.0 mL, 90 mmol) in $CH_2Cl_2$ (90 mL) at room temperature was added trimethylsilyl trifluoromethanesulfonate (100 μL). The mixture was stirred for 2 h and the homogeneous solution was quenched with saturated aqueous $NaHCO_3$ (100 mL). The $CH_2Cl_2$ layer was separated, washed with brine, dried over anhydrous $MgSO_4$ and concentrated in vacuo. Chromatography over silica gel, eluting with ethyl acetate:hexanes (2:5), furnished 10.2 g (79%) of the title compound as a pale yellow solid. $^1$H NMR ($CDCl_3$): δ7.70 (1H, s), 7.68 (1H, s), 4.15 (4H, m), 2.98 (2H, t), 2.38 (2H, t)

Step 7: 5-Nitro-6-(2,4-difluorophenylthio)-1-indanone ethylene ketal

To a mixture of 5-nitro-6-bromo-1-indanone ethylene ketal (600 mg, 2.0 mmol) and 2,4-difluorothiophenol (F. Klages and K. Bott Chem. Ber. 97,735 (1964)) (440 mg, 3.0 mmol) in pyridine (4.0 mL) was added a solution of 8M aqueous potassium hydroxide (375 μL, 3.0 mmol) at room temperature. The mixture was stirred for 2 h, diluted with water and extracted with ethyl acetate. The ethyl acetate extract was washed successively with 1M aqueous NaOH (2x),0.5M aqueous HCl (1x), brine, dried over anhydrous $MgSO_4$ and concentrated in vacuo. Chromatography over silica gel and eluted with toluene: ethyl acetate (10:1) afforded the title compound (590 mg, 81%) as a pale yellow solid.

$^1$H NMR ($CDCl_3$)δ8.12 (s,1H), 7.60 (m, 1H), 7.00 (m, 2H), 6.70 (s, 1H), 4.10–3.90 (m 4H), 2.95 (t, 2H), 2.30 (t, 2H).

Step 8: 5-Amino-6-(2,4-difluorophenylthio)-1-indanone

A mixture of 5-nitro-6-(2,4-difluorophenylthio)-1-indanone ethylene ketal (580 mg, 1.59 mmol), iron powder (500 mg, 8.9 mmol) and ammonium chloride (50 mg, 0.93 mmol) in 30 mL of ethanol:water (2:1) was refluxed for 1 h. The hot mixture was filtered through celite. The solvente was evaporated in vacuo. The residue was diluted with water and extracted with ethyl acetate. The ethyl acetate extract was dried over anhydrous $MgSO_4$ and concentrated to give the title compound (410 mg, 81%) as a light brown solid. $^1$H NMR ($CDCl_3$) δ7.95 (s, 1H), 7.00 (m, 1H), 6.80 (m, 2H), 6.72 (s, 1H), 4.95 (br s, 2h), 3.05 (t, 2H), 2.65 (t, 2H).

Step 9: 5-Methanesulfonamido-6-(2,4-difluorophenylthio)-1-indanone

A mixture of 5-amino-6-(2,4-difluorophenylthio)-1-indanone (400 mg, 1.25 mmol), triethylamine (1.0 mL, 7.2 mmol) and methanesulfonyl chloride (300 μL, 3.9 mmol) in methylene chloride (10 mL) was stirred at room temperature for 1 h. After dilution with more methylene chloride (20 mL), the mixture was washed successively with saturated aqueous sodium bicarbonate, 1M aqueous HC1 and brine. The methylene chloride layer was separated, dried over anhydrous $MgSO_4$ and concentrated to give a dark solid residue.

To a solution of the above residue in MeOH:THF (2:1, 24 mL) at room temperature was added 10M aqueous NaOH (375 μL, 3.75 mmol). The mixture was stirred at room temprature for 30 min and then acidified with 3M aqueous HCl (1.5 mL). The volatile solvents were evaporated in vacuo. The residue was diluted with water, and extracted with ethyl acetate. The ethyl acetate layer was separated, washed with brine, dried over anhydrous $MgSO_4$ and concentrated. Chromatography over silica gel and elution with hexanes: ethyl acetate (1:1) yielded the title compound (350 mg, 76%) as a light brown solid. $^1$H NMR ($CDCl_3$) δ8.05 (s, 1H), 7.98 (s, 1H), 7.78 (s, 1H), 7.30 (m, 1H), 6.88 (m, 2H), 3.16 (t, 2H), 3.06 (s, 3H), 2.70 (t, 2H).

PREPARATION EXAMPLE FOR METHOD B (COMPOUND 17)

4-(2,4-dichlorophenoxy)-3-nitrobenzaldehyde

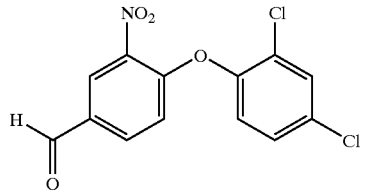

To powdered potassium hydroxide (9.0 g, 0.12 mol) at 110° C. was added 2,4-dichlorophenol (19.0 g, 0.12 mol) in one portion. The mixture was stirred for 15 min. and a homogenous solution resulted. 4-Chloro-3-nitrobenzaldehyde (20.0 g, 0.11 mol) was added and the thick mixture was stirred at 110° C. for 1 h. After cooling to room temperature, the mixture was partitioned between 2M aqueous sodium hydroxide and ethyl acetate. The organic layer was separated, washed with brine and dried over magnesium sulfate. Evaporation of solvent and recrystallization from ethanol afforded 27.0 g (80%) of the title compound as a pale yellow solid. $^1$H NMR ($CDCl_3$) δ9.80 (s, 1H), 8.48 (s, 1H), 7.90 (d, 1H), 7.53 (s, 1H), 7.35 (d, 1H), 7.16 (d, 1H), 6.88 (d, 1H). 3-Amino-4-(2,4-dichlorophenoxy)benzaldehyde

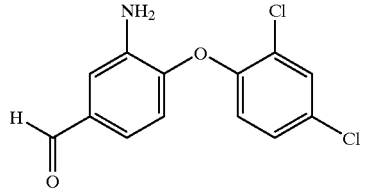

A mixture of 4-(2,4-dichlorophenoxy)-3-nitrobenzaldehyde (19.0 g, 0.006 mol), iron powder (13.0 g, 0.23 mol) and ammonium chloride (saturated aqueous solution, 50 ml) in 600 mL of ethanol:water (2:1) was refluxed for 1.5 h. The hot mixture was filtered through celite. Solvent was evaporated in vacuo. The residue was partitioned between dichloromethane and water. The organic layer was separated, dried over anhydrous magnesium sulfate and concentrated. Chromatography over silica gel and elution with hexanes:ethyl acetate (2:1) gave the title compound (10.0g, 60%) as a white solid. $^1$H NMR ($CDCl_3$) δ9.83 (s, 1H), 7.50 (s, 1H), 7.33 (s, 1H), 7.25 (d, 1H), 7.15 (d, 1H), 7.00 (d, 1H), 6.68 (d, 1H), 4.1 (brs, 2H).

4-(2,4-Dichlorophenoxy)-3-methanesulfonamidobenzaldehyde

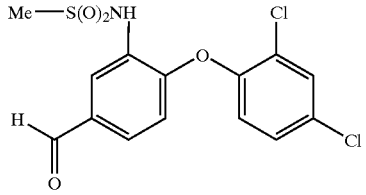

A mixture of 3-amino-4-(2,4-dichlorophenoxy) benzaldehyde (8.0 g, 0.028 mol), trietylamine (15.8 mL, 0.11 mol) and methanesulfonyl chloride (9.75 g, 0.085 mol) in dichloromethane (200 mL) was stirred at 0° C. for 1 h. The mixture was then washed with saturated aqueous sodium bicarbonate, dried over anhydrous magnesium sulfate and concentrated to give a dark solid residue.

To a solution of the above residue in MeOH:THF (2:1,150 mL) at 0° C. was added 2M aqueous sodium hydroxide (42 mL, 84 mmol). The mixture was stirred at room temperature for 1 h and then acidified with 1M aqueous hydrochloric acid. Most of the organic solvents-were evaporated in vacuo. The residue was extracted with ethyl acetate, washed with brine, dried over anhydrous magnesium sulfate and concentrated. The solid residue was suspended in ethanol and filtered to give the title compound. The filtrate was concentrated and chromatographed over silica gel with hexanes-:ethyl acetate (2:1) to give the title compound (14.0 g, 92% combined yield) as a white solid. $^1$H NMR ($CDCl_3$) δ9.90 (s, 1H), 8.13 (s, 1H), 7.58 (d, 1H), 7.53 (s, 1H), 7.35 (d,1H), 7.11 (d, 1H), 7.03 (brs, 1H), 6.68 (d, 1H), 3.12 (s, 3H).

Ethyl 4-(2,4-dichlorophenoxy)-3-methanesulfonamido-cinnamate

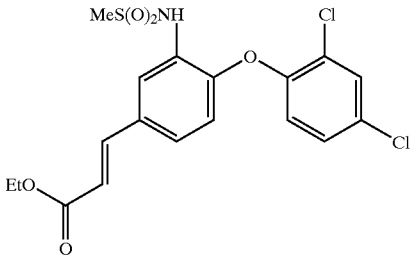

To a suspension of sodium hydride (500 mg, 16.7 mmol) in tetrahydrofuran (15 mL) was added dropwise triethylphosphonoacetate (1.87 g, 8.3 mmol) at 0° C. The mixture was stirred at 0° C. for 15 min. and a homogeneous solution resulted. A solution of 4-(2,4-dichlorophenoxy)-3-methanesulfonamido-benzaldehyde (2.5 g, 6.94 mmol) in tetrahydrofuran (20 mL) was added slowly. After stirring at room x s temperature for 2 h, the mixture was quenched with acetic acid (1mL). Solvent was evaporated in vacuo. The residue was diluted with water and extracted with ethyl acetate. The ethyl acetate layer was separated, washed with water, brine, dried over anhydrous magnesium sulfate and concentrated. Chromatography over silica gel and elution with hexanes:ethyl acetate (3:1) yielded the title compound (2.57 g, 86%) as a solid. $^1$H NMR ($CDCl_3$)δ7.82 (s, 1H), 7.60 (d, 1H), 7.50 (s, 1H), 7.30 (d, 1H), 7.18 (d, 1H), 7.04 (d, 1H), 6.89 (s, 1H), 6.60 (d, 1H), 6.36 (d, 1H), 4.25 (q, 2H) 3.08 (s, 3H), 1.30 (t, 3H).

Ethyl 3-[4-(2,4-dichlorophenoxy)-3-methanesulfonamido] phenylpropionate

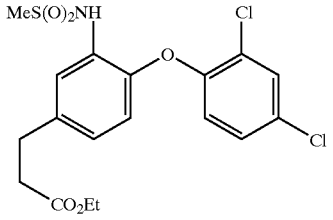

A mixture of ethyl 4-(2,4-dichlorophenoxy)-3-methanesulfonamido-cinnamate (2.2 g, 5.1 mmol) and 10% palladium on Charcoal (850 mg) in ethyl acetate (75 mL) was hydrogenated at room temperature under 30 psi of hydrogen atmosphere for 2 h. The catalyst was filtered off and the tiltrate was concentrated to give the title compound (2.1 g, quantitative yield). $^1$H NMR ($CDCl_3$) δ7.40 (s, 2H), 7.22 (d, 1H), 6.95 (d, 1H), 6.90 (d, 1H), 6.82 (brs, 1H), 6.59 (d, 1H), 4.08 (q, 2H), 3.0 (s, 3H), 2.90 (t, 2H), 2.59 (t, 2H), 1.22 (t, 3H).

3-[4-(2,4-Dichlorophenoxy)-3-methanesulfonamido] phenylpropionic acid

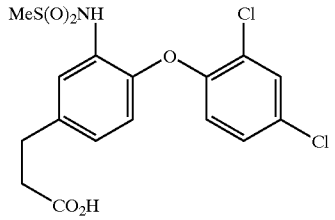

To a solution of ethyl 3-[4-(2,4-dichlorophenoxy-3methanesulfonamido]phenylpropionate (2.1 g, 5.0 mmol) in ethanol (70 mL) was added an aqueous solution of 2 M sodium hydroxide (6.0 mL, 12 mmol). The mixture was stirred at 45° C. for 2 h and acidified with acetic acid. Solvent was removed in vacuo. The residue was diluted with water and extracted with ethyl acetate. The ethyl acetate layer was separated, washed successively with water, brine, dried over anhydrous magnesium sulfate and concentrated. Chromatography over silica gel and elution with hexanes-:ethyl acetate (3:1) with 2% acetic acid yielded the title compound (1.7 g, 84%) as a white solid. $^1$H NMR ($CDCl_3$) δ7.51 (s, 1H), 7.48 (s, 1H), 7.24 (d, 1H), 6.96 (d, 1H), 6.92 (d, 1H), 6.78 (brs, 1H), 6.60 (d, 1H), 3.02 (s, 3H), 2.93 (t, 2H), 2.68 (t, 2H).

5-Methanesulfonamido-6-(2,4-dichlorophenoxy)-1-indanone

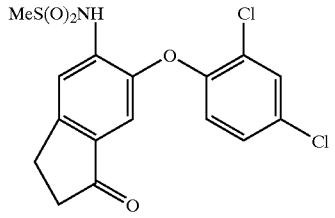

To a mixture of 3-[4-(2,4-dichlorophenoxy)-3-methanesulfonamido]phenylpropionic acid (1.2 g, 3.0 mmol) and N,N-dimethylformamide (1 drop) in dichloromethane (12 mL) at 0° C. was added dropwise oxalyl chloride (785 mg, 6.2 mmol). The mixture was stirred for 30 min. and solvent was evaporated in vacuo to give a foam.

The above foam residue was dissolved in anhydrous 1,2-dichloroethane (10 mL). Aluminum trichloride anhydrous (1.2 g, 9.0 mmol) was added portionwise at 0° C. The mixture was stirred at room temperature for 30 min. and 1M aqueous hydrochloric acid was added. The whole mixture was extracted twice with dichloromethane. The combined organic extracts were washed successively with water, brine, dried over anhydrous magnesium sulfate and concentrated. Chromatography over silica gel and elution with hexanes-:ethyl acetate (2:1) afforded a solid residue. Recrystallization from ethanol yielded the title compound (870 mg, 75%) as white needles. $^1$H NMR ($CDCl_3$) δ7.73 (s, 1H), 7.50 (s, 1H), 7.32 (m, 2H), 7.08 (d, 1H), 6.90 (s, 1H), 3.14 (s, 3H), 3.10 (t, 2H), 2.68 (t, 2H).

What is claimed is:

1. A compound of the formula I

I

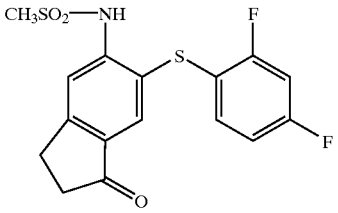

or a pharmaceutically acceptable salt thereof.

2. A method of selectively inhibiting cyclooxygenase-2 comprising administration to a patient in need of such treatment a non-toxic therapeutically effective amount of a compound according to claim 1.

3. A method of treating a cyclooxygenase-2 mediated disease in patients having a history of a gastro-intestinal disorder comprising administration to a patient in need of such treatment a non-toxic therapeutically effective amount of a compound according to claim 1.

[4. A method of selectively inhibiting cyclooxygenase-2 comprising administration to a patient in need of such treatment a non-toxic therapeutically effective amount of a compound according to claim 1.]

*5. A method for selectively inhibiting cyclooxygenase-2activity in a human host, comprising administering a non-steroidal compound that selectively inhibits activity of the cyclooxygenase-2 gene product to a human host in need of such treatment, wherein said non-steroidal compound is a compound of the formula I*

I

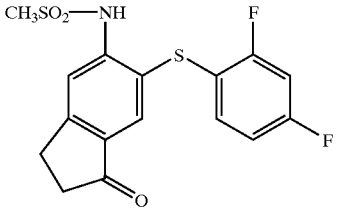

*or a pharmaceutically acceptable salt thereof.*

*6. The method of claim 5, wherein the compound of formula I is administered at a dosage of from about 0.01 mg to about 140 mg per kilogram of body weight per day.*

*7. The method of claim 5, wherein the compound of formula I is administered in an amount from about 1 mg to about 1000 mg.*

* * * * *